(12) United States Patent
Anschutz et al.

(10) Patent No.: US 8,286,514 B2
(45) Date of Patent: Oct. 16, 2012

(54) CONDUCTIVITY CELL PISTON EXTRACTOR AND METHOD

(75) Inventors: Don A. Anschutz, Houston, TX (US); Allan R. Rickards, Tomball, TX (US); Cole J. Chavey, Houston, TX (US)

(73) Assignee: Prop Tester, Inc., Cypress, TX (US)

( * ) Notice: Subject to any disclaimer, the term of this patent is extended or adjusted under 35 U.S.C. 154(b) by 484 days.

(21) Appl. No.: 12/608,236

(22) Filed: Oct. 29, 2009

(65) Prior Publication Data

US 2011/0100113 A1 May 5, 2011

(51) Int. Cl.
*G01N 17/00* (2006.01)
(52) U.S. Cl. ...................................... 73/865.6
(58) Field of Classification Search .............. 73/865.6, 73/866
See application file for complete search history.

(56) References Cited

U.S. PATENT DOCUMENTS

| | | | |
|---|---|---|---|
| 2,910,270 A * | 10/1959 | Schultz | 254/98 |
| 4,791,822 A * | 12/1988 | Penny | 73/865.6 |
| 4,848,145 A | 7/1989 | Blaschke et al. | |
| 5,018,396 A | 5/1991 | Penny | |
| 5,226,310 A | 7/1993 | Steiger | |
| 5,285,692 A | 2/1994 | Steiger et al. | |
| 2007/0079961 A1 | 4/2007 | Morgan et al. | |
| 2008/0060444 A1 * | 3/2008 | Conway et al. | 73/821 |
| 2009/0306898 A1 | 12/2009 | Anschutz et al. | |

\* cited by examiner

*Primary Examiner* — Hezron E Williams
*Assistant Examiner* — Nathaniel Kolb
(74) *Attorney, Agent, or Firm* — Streets & Steele (57) ABSTRACT

Embodiments of the invention include a proppant testing apparatus with a portable piston extractor and related methods. In one embodiment, a testing apparatus includes a test cell body in which an upper piston is constrained to vertically reciprocate within a test cavity. A laterally-extending width bar is coupled to the piston above the test cell body. A portable piston extractor is provided for freeing the stuck piston following testing. The piston extractor includes an extractor base removably supported on the test cell body and an extractor arm movably coupled to the extractor base. A drive mechanism is configured for driving the extractor arm into vertical engagement with the width bar, to raise the piston for extraction. In another embodiment, a set of gear boxes interconnected by shafts may be used to apply a uniform separation force between the piston and test cell body.

18 Claims, 6 Drawing Sheets

CONDUCTIVITY CELL PISTON EXTRACTOR AND METHOD

BACKGROUND

1. Field of the Invention

The present invention relates to proppant testing methods and apparatuses.

2. Background of the Related Art

Oil and natural gas are produced from wells having porous and permeable subterranean formations. The porosity of the formation permits the formation to store oil and gas, and the permeability of the formation permits the oil or gas fluid to move through the formation. Sometimes the permeability of the formation is insufficient for economic recovery of oil and gas. In other cases, during operation of the well, the permeability of the formation drops to such an extent that further recovery becomes uneconomical. In such circumstances, it is common to fracture the formation and prop the fracture in an open condition using a particulate material known as a proppant.

Fracturing is usually accomplished by hydraulic pressure using fluids such as water, water viscosified with polysaccharides, and other polymers, crosslinked polysaccharides, or hydrocarbon-based, gel-like fluid. The hydraulic pressure is increased until cracks or fissures form in the underground rock. The proppant particles, which are suspended in this pressurized fluid, are forced into the cracks. The proppant particles prop open the formed cracks so the cracks remain open when the hydraulic pressure is reduced. The oil or gas is then able to flow through the interstices between the particles to increase economic recovery. The oil or gas flows to collection regions and is pumped to the surface.

A wide variety of materials are used as proppants. Typical proppant materials include sand, glass beads, and ceramic pellets. The proppant used during a fracturing operation may be selected according to the geological conditions of the formation to be fractured. The physical properties of a particular proppant material determine its effectiveness. The particle size of a proppant, for example, affects the permeability of the fractured formation, and the corresponding ability for hydrocarbons to flow through the proppant pack. The crush strength of the proppant provides an indication of how well the proppant resist the crushing subterranean forces while propping open a fracture. Over time, the pressure of the surrounding rock tends to crush the proppants, resulting in reduced particle size, which reduces permeability. Very fine proppant particles referred to as "fines" may result from crushing. Fines tend to migrate and plug the interstitial flow passages in the propped structure. These migratory fines drastically reduce the permeability, lowering the conductivity of the oil or gas.

The importance of the physical properties of proppants is well recognized in the industry. The American Petroleum Institute (API) has issued Recommended Practices for proppant testing. For example, API Recommended Practices RP-19C covers testing procedures for sand used in hydraulic fracturing operations. These Recommended Practices include testing procedures for determination of properties that include particle size and crush resistance. International Standard ISO 13503-2 "Petroleum and natural gas industries-Completions fluids and materials-Part 2: Measurement of properties of proppants used in hydraulic fracturing and gravel-packing operations" also governs this testing.

Proppants are commonly tested above ground, such as in a laboratory, under conditions of pressurized fluid flow in combination with a crushing level of force, to simulate subterranean formation conditions. To test a proppant under such conditions, a proppant sample is typically placed in the cavity of a pressure vessel and trapped within the cavity between a cavity wall and a piston. In this context, the proppant sample may be referred to as a "proppant pack." The piston is driven against the proppant pack with a crushing level of force, often in combination with flowing pressurized fluid through the cavity and the proppant pack. The forces and pressures involved in proppant testing can result in the piston becoming stuck within the vessel. The piston must be removed from the vessel before the proppant can be removed for analysis. However, there is conventionally no easy way to free a stuck piston from a vessel.

BRIEF SUMMARY

Embodiments of the invention include a piston extractor for a conductivity test cell, a method of extracting a piston from a conductivity test cell body, and a proppant test apparatus including a cooperating piston extractor. In one example embodiment, a proppant testing apparatus includes a test cell body having an upper exterior surface, a lower exterior surface, and a test cavity extending through at least the upper exterior surface. An upper piston is constrained to vertical reciprocation within the test cavity. A laterally-extending width bar is coupled to the piston above the test cell body. A portable piston extractor includes an extractor base removably supportable on the test cell body, an extractor arm movably coupled to the extractor base, and a drive mechanism configured for driving the extractor arm into vertical engagement with the width bar.

DETAILED DESCRIPTION

Embodiments of the invention include a proppant testing apparatus with a portable piston extractor, and related methods, for extracting a stuck piston. The proppant testing apparatus may include, for example, a conductivity cell for conductivity-testing a proppant sample. A test cell body with a stuck piston may be removed from a test fixture and placed on a working surface. The piston extractor is easily placed by hand in a supported position on the test cell body. A threaded drive member may be actuated, such as using a wrench, to raise an extractor arm included with the piston extractor. The extractor arm urges the piston upward to free the stuck piston. As a result, the stuck piston may be extracted more efficiently and with much less risk for damage than with conventional approaches of prying or hammering a piston from a test cell body. The proppant testing apparatus and method presented below increase the speed, reliability, ease, and quality of performing proppant testing and post-testing analysis, with associated cost savings.

Figure 1:
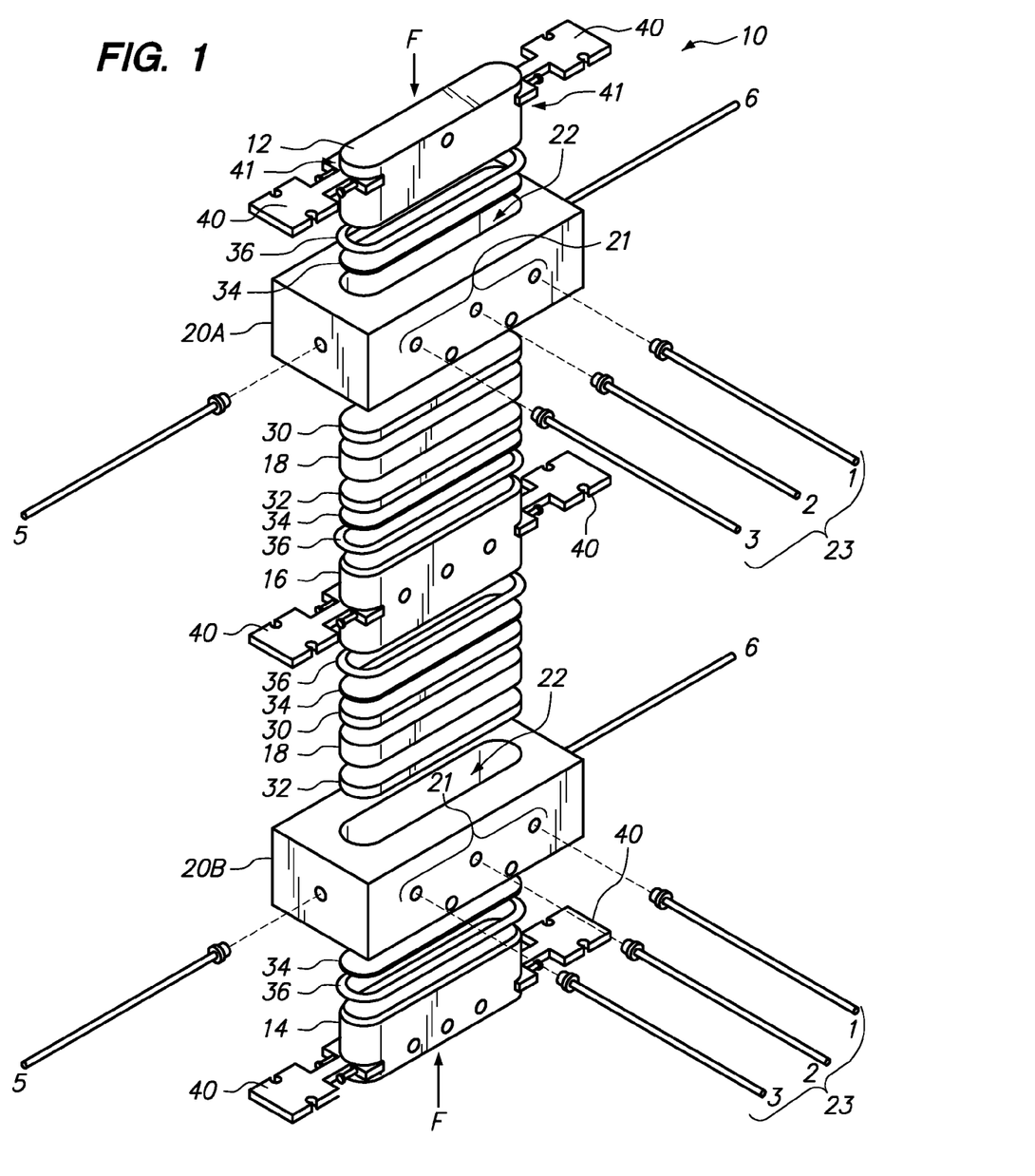
FIG. 1 is an exploded perspective view of an example proppant testing apparatus including a stack of two test cell bodies.

FIG. 1 is an exploded perspective view of an example of a proppant testing apparatus 10 for testing a proppant under conditions of pressurized fluid flow and a proppant-crushing level of force "F." The testing apparatus 10 in this embodiment includes a stack of two test cell bodies 20, individually identified in this view as a first test cell body 20A stacked above a second test cell body 20B. A testing apparatus used in accordance with another embodiment of the invention may include between one and four test cell bodies, although a stack of two or more test cell bodies allows multiple proppant samples 18 to be simultaneously tested under a load applied by a single compression testing fixture (not shown). The testing apparatus 10 further includes a first piston 12, a second piston 14, and a third piston 16 between the first and second pistons 12, 14. The first piston 12 serves as an "upper piston" to the test cell body 20A. The second piston 14 serves as a "lower piston" to the test cell body 20B. The third piston 16 simultaneously serves as a lower piston to the test cell body 20A above it and as an upper piston to the test cell body 20B below it.

A proppant sample 18, alternatively referred to as a proppant pack 18, is captured in each of the test cell bodies 20 between an upper compression die 30 and a lower compression die 32. The compression dies 30, 32 are typically made of sandstone, and are formed with an outer profile closely matching the interior profile of each test cell cavity 22. Metal shims 34 and seals 36 are provided between the outer profile of the compression dies 30, 32 and the interior profile of each test cell cavity 22 to seal and contain the proppant packs 18 between the compression dies 30, 32 and the cavity walls 22. The seal 36 may be, for example, a Tetraseal® sealing ring or other elastomeric seal known in the art.

Multiple pressure ports, generally indicated at 21, are provided on the test cell bodies 20. The pressure ports 21 include, by way of example, a low pressure port 1, a thermocouple port 2, and a high pressure port 3 to determine the differential pressure as fluid is pumped through the proppant pack 18. The thermocouple ports 2 are included for inserting a thermocouple (not shown) to take temperature readings during testing. The pressure ports 21 are in fluid communication with the respective test cell cavities 22. Pressure fittings 23 are sealingly connected to the pressure ports 21, typically by a threaded connection between each pressure fitting 23 and pressure port 21. Fluid pressure may be supplied to the pressure fittings 23 to pressurize the cavities 22 during testing. An inlet port 5 and a back-pressure port 6 are also provided. Fluid may be pumped into the test cavity 22 through the inlet port 5 and out of the test cavity 22 through the back-pressure port 6 to simulate the flow of formation fluid through the proppant in the proppant pack 18. A system of valves and pressurized fluid supply lines may be controlled, as known in the art, to provide pressurized fluid flow. Back-pressure may be applied at the back-pressure port 6 to increase fluid pressure within the test cavity 22.

Laterally extending arms (alternatively referred to as "width bars" in the field of proppant testing) 40 are secured to each of the upper, lower, and intermediary pistons 12, 14, 16 at slots 41. The laterally extending width bars 40 may be engaged by a piston extractor (as discussed below) to free a stuck upper piston. The width bars 40 in this embodiment also serve as reference locations for measuring cylinder displacement as a result of proppant crush testing. The distance between the width bars 40 may be measured both before and after testing to assist in determining how much the proppant packs 18 have been compressed.

Under the high compressive forces and fluid pressures applied to the test cavities 22 during testing, the seal 36 forms mechanical bonds with the inner walls of the test cell cavities 22, which can cause the pistons 12, 14, 16 to become temporarily stuck within the respective test cell bodies 20. An embodiment of the invention is directed to a portable piston extractor and related method for freeing a stuck piston following proppant testing. The piston extractor may be included with such a testing apparatus, and is configured to cooperate with elements of the testing apparatus to free the stuck piston.

Figure 2:
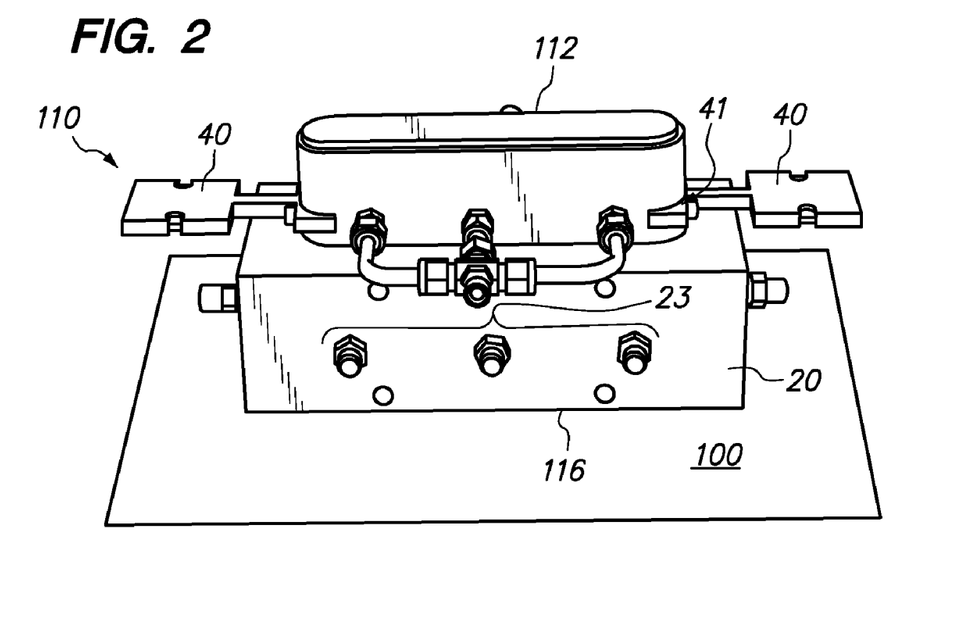
FIG. 2 is an assembled, perspective view of another example testing apparatus consisting of a single, stackable test cell body.

FIG. 2 is an assembled, perspective view of a testing apparatus 110 according to an embodiment of the invention. The testing apparatus 110 may be a sub-assembly of the testing apparatus 10 of FIG. 1. An upper piston 112 has been positioned within the test cell body 20 from above, and a lower piston 116 has been positioned within the test cell body 20 from below the test cell body 20. Width bars 40 are coupled to the piston 112 above the test cell body 20, at slots 41. Pressure fittings 23 are arranged horizontally on the test cell body 20. The lower piston 116 is positioned on a working surface 100, with the weight of the testing apparatus 110 supported on the lower piston 116. The working surface 100 may be, for example, the surface of a testing bench or laboratory bench, the floor, a tabletop, or other surface that can support the weight of the testing apparatus 110 during removal of the upper piston 112. The lower piston 116 extends below the test cell body 20 so that the test cell body 20 is supported above the working surface 100.

Figure 3:
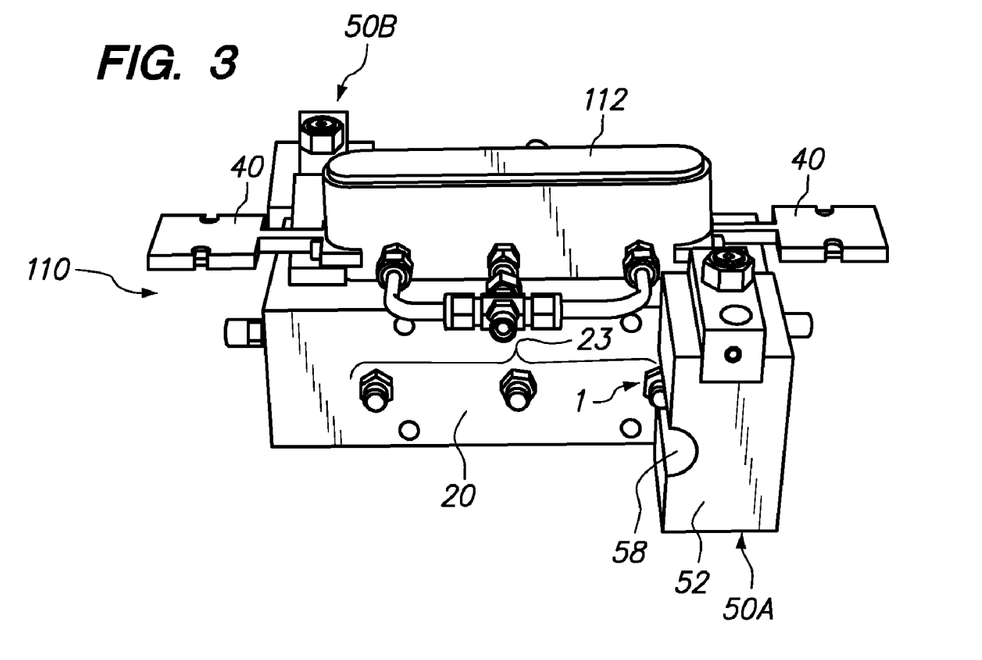
FIG. 3 is another perspective view of the example testing apparatus of FIG. 2, including a pair of piston extractors.

FIG. 3 is another perspective view of the testing apparatus 110 of FIG. 2, including a pair of piston extractors (50) individually referred to as 50A, 50B. The piston extractors 50A, 50B are configured to cooperate with specific other features of the testing apparatus 110 to free the upper piston 112 when stuck. The piston extractors 50 may be operated, as described below, to safely and easily separate the upper piston 112 from the test cell body 20, with minimal mechanical effort on the part of the user. The piston extractor 50 provide a convenient alternative to hammering or otherwise prying apart the stuck upper piston 112 and test cell body 20, which may otherwise damage components of the testing apparatus 110.

The pressure ports 21 are used in the measurement of differential pressure as fluid is flowed through the proppant pack 18. Conductivity is then determined, as known in the art, as the product of fluid flow rate, viscosity, and area of flow, divided by the product of differential pressure and length. The row of pressure ports 21 are spaced 5.0 inches apart, as mandated by ISO regulations. As a consequence of this mandated spacing between pressure ports 21, the pressure fittings 23, which project outwardly from the test cell body 20, span a wide portion of the length of the test cell body 20. The relatively wide spacing of the pressure fittings 23 positions the pressure fitting 23 at pressure port 1 very close to an end of the test cell body 20.

The piston extractors 50A, 50B are removably positioned at locations selected to allow maximum upward force without damage to the width bars 40. In one aspect, the piston extractors 50A, 50B are positioned inwardly, close to the piston 112, to minimize the risk of bending the width bars 40. The design and positioning of the piston extractors 50A, 50B is also tailored to accommodate the particular structure of other elements of the testing apparatus 110. The extractor 50A, for example, avoids interference with the pressure fitting 23 at port 1, due to the particular placement of the piston extractor 50A along the test cell body 20 and with the inclusion of an arcuate cutaway 58 on the extractor body 52. The arcuate cutaway 58 provides clearance between the extractor body 52A and the pressure fitting 23 at port 1. The other extractor 50B is partially obscured from the view of FIG. 3, but may be similarly positioned and configured with a cutaway (not shown) to avoid another pressure fitting on the opposite side of the test cell body 20.

Figure 4:
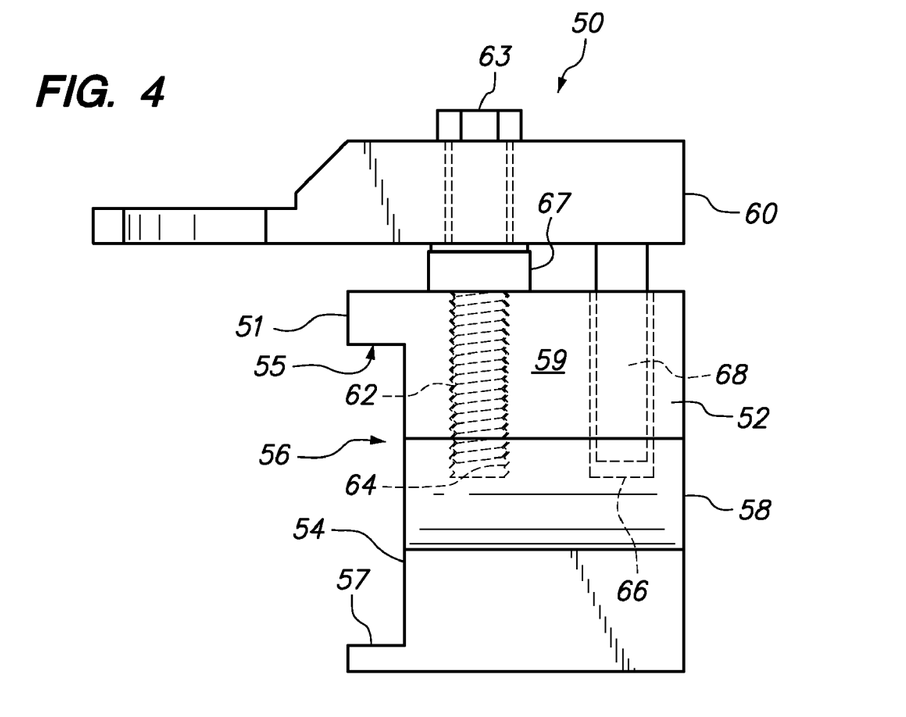
FIG. 4 is a side elevation view of the piston extractors in further detail.

FIG. 4 is a side elevation view of one of the piston extractors 50 in further detail. The extractor base 52 has an external, C-shaped channel 56 on a first side 51 of the extractor base 52. As explained further below, the channel 56 fits closely around an exterior portion of a test cell body and allows the extractor base 52 to be removably supported on the test cell body. The channel 56 includes an upper flange 55 and a lower flange 57 at opposite ends of a web 54. The arcuate cutaway 58 used to avoid interference with one of the pressure fittings 23 (see FIG. 3) is provided on a second side 59 of the extractor base 52, oriented perpendicular to the first side 51. The cutaway 58 is approximately midway along the web 54 between the upper flange 55 and the lower flange 57.

A rigid extractor arm 60 is movably connected to the extractor base 52. The extractor arm 60 is driven relative to the extractor base 52 using a drive mechanism that includes a male threaded member 62 and a female threaded member 64. The male threaded member 62 is rotatably connected to the extractor arm 60 and threadedly connected to the female threaded member 64. A head 63 of the male threaded member 62 is provided as a location of rotational engagement by a tool. For example, the male threaded member 62 is illustrated in the figures as a bolt, wherein the head 63 is a bolt-head that can be rotationally engaged by a wrench. The extractor arm 60 is sandwiched between the head 63 and a collar 67 to allow rotational movement between the male threaded member 62 and the extractor arm 60 while preventing relative axial movement between the extractor arm 60 and the male threaded member 62. Rotating the male threaded member 62 drives the extractor arm 60 vertically with respect to the extractor base 52. Rotating the male threaded member 62 in one rotational direction raises the extractor arm 60 with respect to the extractor base 52, while rotating the male threaded member in the opposite rotational direction lowers the extractor arm 60 with respect to the extractor base 52. The extractor arm 60 is shown in a fully-lowered position in FIG. 3.

A guide hole 66 is provided in the extractor base 52, parallel to and laterally spaced from the male threaded member 62. A guide pin 68 is fixed to the extractor arm 60. The guide pin 68 is slidingly received within the guide hole 66 on the extractor base 52. The guide pin 68 moves vertically with the extractor arm 60 when the extractor arm 60 is raised or lowered. The guide pin 68 is guided within the guide hole 66 throughout the range of movement of the extractor arm 60, to prevent rotation of the extractor arm 60 about the axis of the drive member 62.

Figure 5:
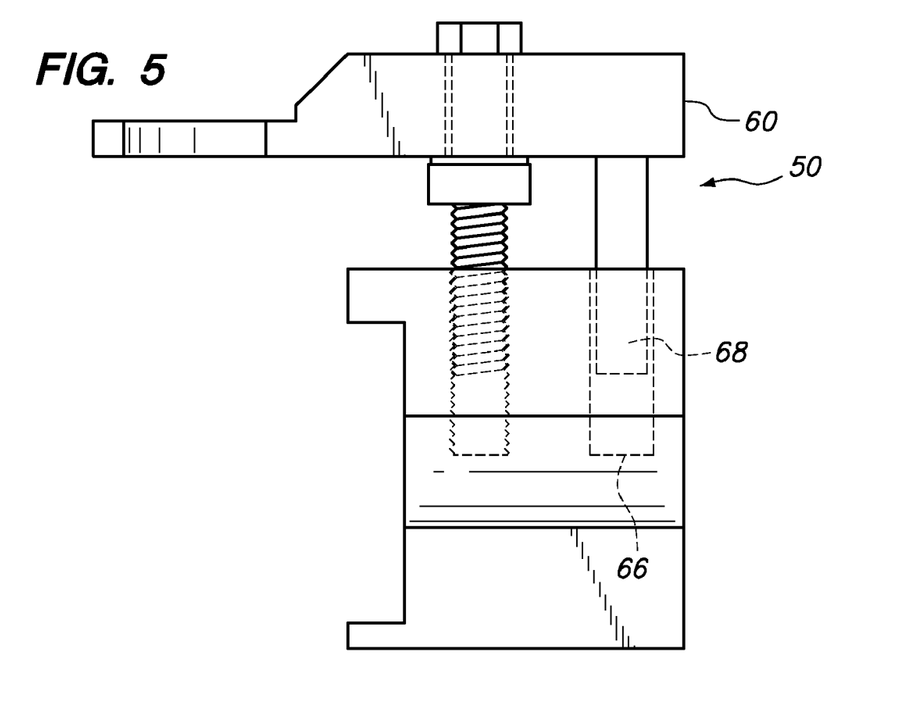
FIG. 5 is a side elevation view of the piston extractor with the extractor arm moved from the fully-lowered position of FIG. 4 to an upper position.

FIG. 5 is another side elevation view of the piston extractor 50 of FIG. 4, with the extractor arm 60 moved from the fully-lowered position of FIG. 4 to an upper position, in response to rotation of the threaded member 63. The mating of the guide pin 68 with the guide hole 66 prevents any appreciable rotation between the extractor arm 60 and the extractor base 62 that might otherwise be caused by rotating the male threaded member 62. The cooperative relationship between the male threaded member 62 and the female threaded member 64, along with the cooperative relationship of the guide pin 68 and guide hole 66, constrains the extractor arm 60 to vertical translation in response to rotation of the male threaded member 62.

Figure 6:
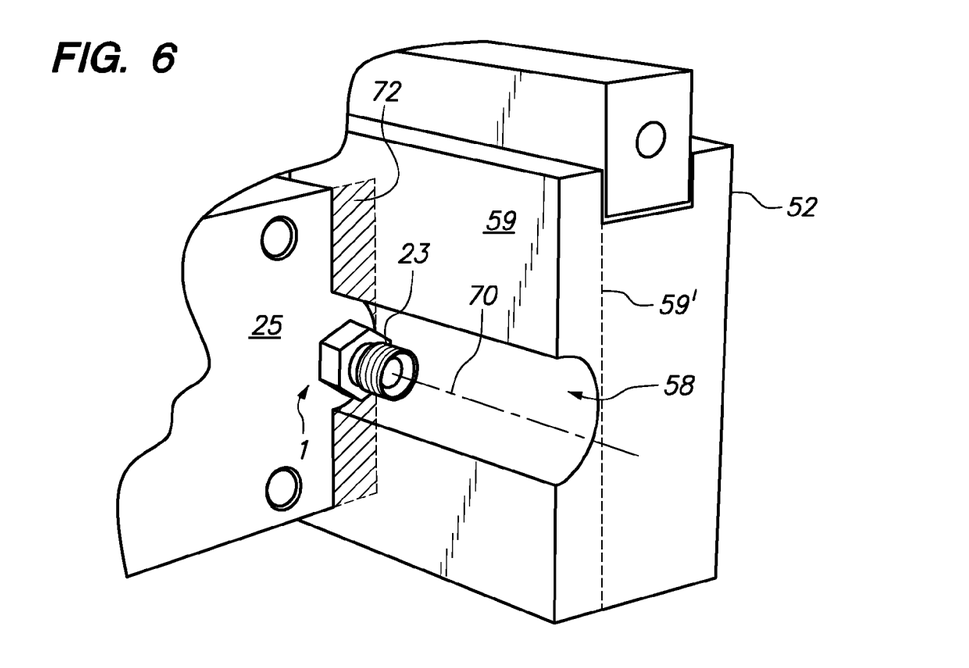
FIG. 6 is a perspective view of the testing apparatus showing an arcuate cutaway for avoiding a pressure fitting.

FIG. 6 is a perspective view of the testing apparatus 110 showing the arcuate cutaway 58 in closer detail. The cutaway 58 receives the pressure fitting 23 at pressure port 1, allowing the extractor base 52 to extend beyond the pressure fitting 23 without interference between the extractor base 52 and the pressure fitting 23. Although not strictly required, the arcuate cutaway 58 in this embodiment is coaxial (shares an axis 70) with the pressure fitting 23, which is a space-efficient shape. The cutaway 58 allows the second side 59 of the extractor base 52 to extend beyond the pressure fitting 23 to provide greater contact area between the extractor base 52 and an outer surface 25 of the test cell body 20. This additional contact area, indicated by a hashed area 72, provides greater stability than without the cutaway 58, which would otherwise require the extractor base to stop at alternate second-wall location 59'.

Figure 7:
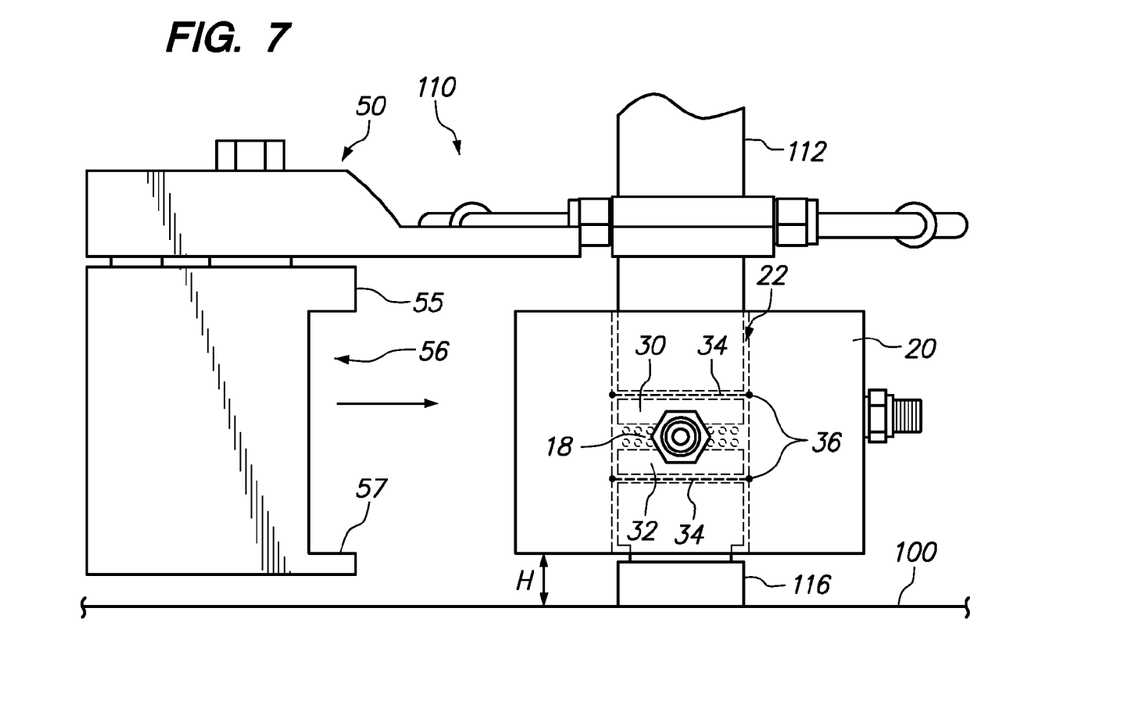
FIG. 7 is a side view of the testing apparatus prior to supporting the piston extractor on the test cell body.
Figure 8:
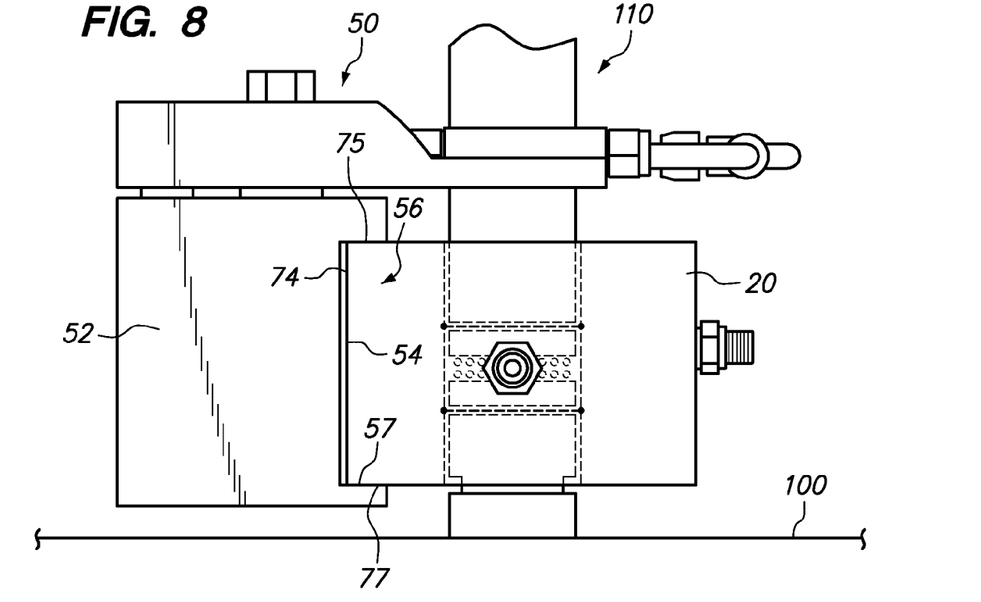
FIG. 8 is a side view of the testing apparatus with the piston extractor in a supported position on the test cell body prior to extracting the piston.
Figure 9:
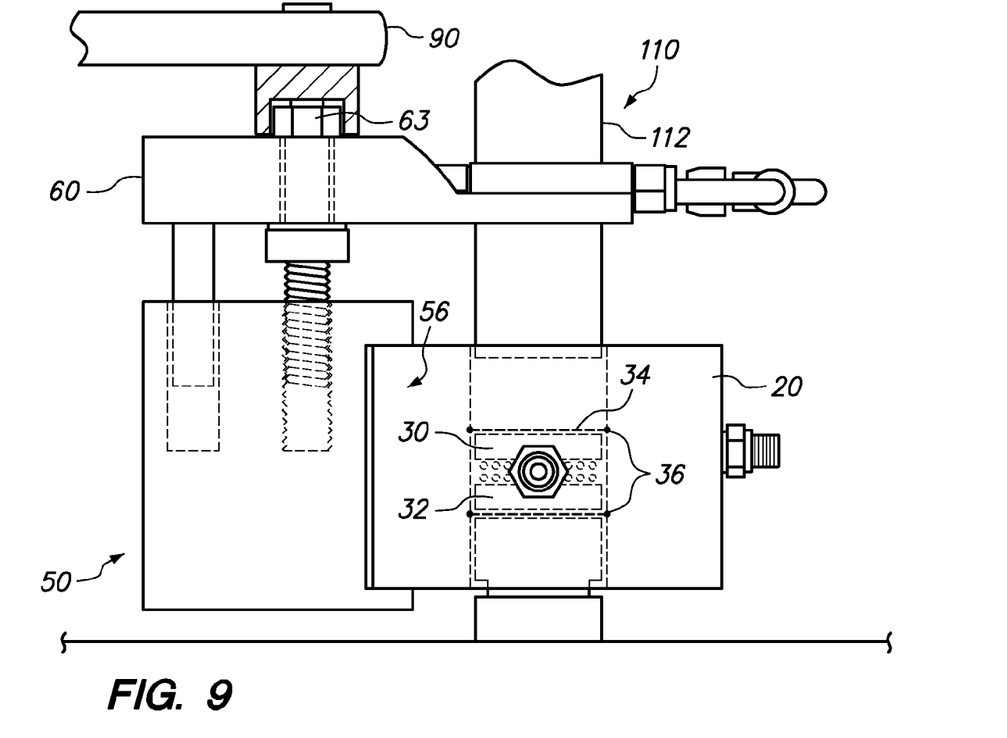
FIG. 9 is a side view of the testing apparatus with the piston extractor raised to free the stuck piston for extraction from the test cell body.

FIGS. 7-9 illustrate a sequence of freeing a presumably stuck cylinder 112 from the test cell body 20 after testing, using the piston extractor 50. The testing apparatus 110 (having a single test cell body 20) may be a subassembly removed from a testing apparatus having a stack of test cell bodies (not shown). The testing apparatus 110 has been removed from a test fixture (not shown) after proppant testing, as a result of which the piston 112 has become stuck due to the high pressures and proppant-crushing level of force.

FIG. 7 is a side view of the testing apparatus 110 before the piston extractor 50 is supported on the test cell body 20. The piston extractor 50 may be held in the position shown by hand, slightly above the working surface 100. The lower piston 116 is shown resting on the working surface 100, and supports the test cell body 20 above the working surface 100 with a clearance height "H." The piston extractor 50 will be moved laterally into a supported position on the test cell body 20, with the channel 56 receiving the test cell body 20.

Dashed lines are used to indicate some of the details inside the test cavity 22. The proppant pack 18 is sandwiched between the upper compression die 30 and the lower compression die 32. The proppant pack 18 is centered at the outlet port 6 (and inlet port 4, not shown), to direct fluid flow through the proppant pack 18 and between the upper compression die 30 and the lower compression die 32 during the testing. The seal 36 has been deformed slightly under pressure, and has formed a mechanical bond with the inner wall of the test cavity 22, causing the upper piston 112 to become stuck.

FIG. 8 is a side view of the testing apparatus 110 with the piston extractor 50 having been moved from its position of FIG. 7 to a supported position on the test cell body 20. The C-shaped channel 56 closely follows the profile of the exterior portion of the test cell body 20, allowing the channel 56 to fit closely about the test cell body 20. The upper flange 55 is in close proximity to an upper exterior surface 75 of the test cell body 20, the lower flange 57 is in close proximity to a lower exterior surface 77, and the web 54 is pushed firmly against a side 74 of the test cell body 20, which supports the extractor base 52 on the test cell body 20. The clearance height H (see FIG. 7) allows the lower flange 57 of the channel 56 to fit between the working surface 100 and the bottom 76 of the test cell body 20. The extractor base 52 is easily positioned on and removed from the test cell body 20 by hand, without having to lift the test cell body 20 away from the working surface 100.

FIG. 9 is a side view of the testing apparatus 110 with the piston extractor 50 raised to free the stuck piston 112 for extraction from the test cell body 20. The male threaded member 62 has been rotated by a hand-operated tool ("wrench") 90. The wrench 90 rotationally engages the head 63 to urge the extractor arm 60 upwardly against the stuck piston. The wrench 90 provides a mechanical advantage for rotating the male threaded member 62. An extractor 50A, 50B may positioned at each end of the test cell body 20 (as in FIG. 3), so that the extractor arm 60 of each extractor 50A, 50B may be alternatively advanced a small amount each time, to progressively raise the piston 112. While the extractor arm 60 is driven to free the stuck piston 112, the positioning of the test cell body 20 in the channel 56 reliably supports the extractor 50 on the test cell body 20. After the piston 112 is free, the male threaded member 62 may be rotated a small amount in a rotational direction opposite the rotational direction used to raise the extractor arm 60, to relieve any forces between the extractor 50 and the piston 112. The extractor 50 may then be easily removed by hand from the test cell body 20.

Figure 10:
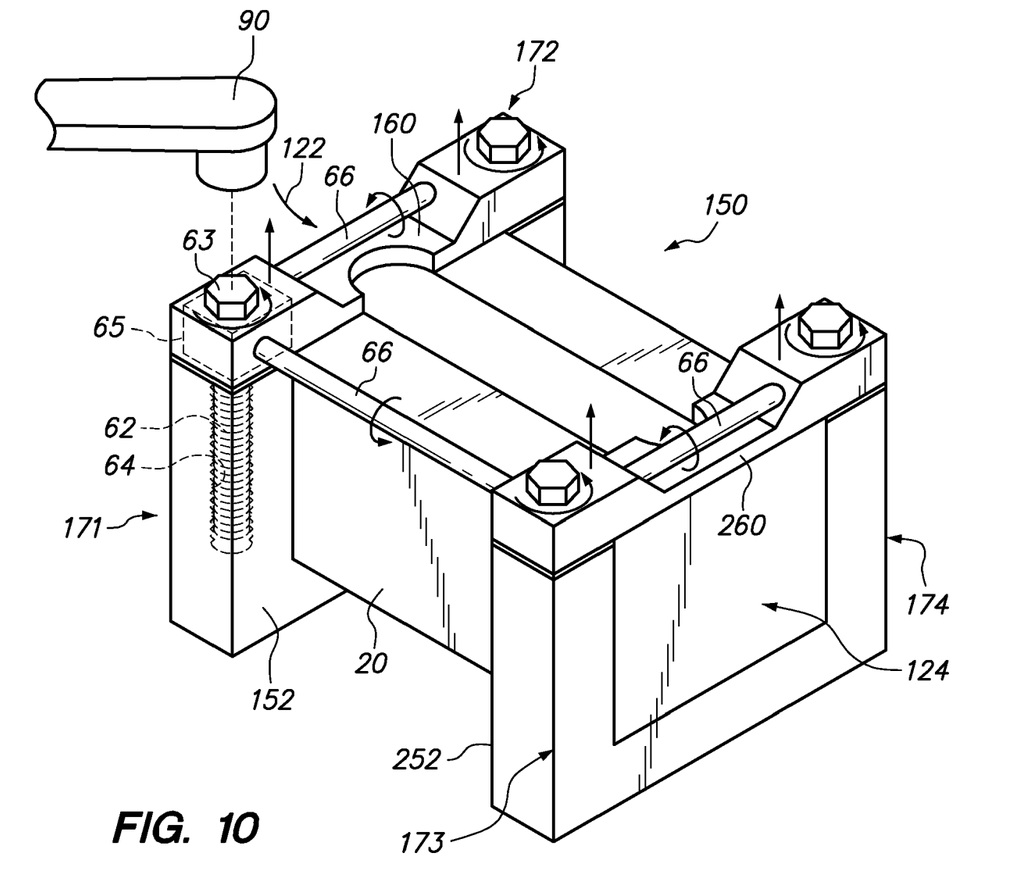
FIG. 10 is a perspective view of a piston extractor according to another embodiment of the invention for providing a uniform separation force between the test cell body and a piston in response to rotating a wrench at a single location of application.

FIG. 10 is a perspective view of a piston extractor 150 according to another embodiment of the invention for providing a uniform separation force between the test cell body 20 and a piston (omitted for ease of illustration) in response to rotating a wrench at a single location of application. The piston extractor 150 includes a first extractor base 152 removably positioned at a first end 122 and an opposing second extractor base 252 removably positioned at the opposite end 124. A first extractor arm 160 is threadedly secured to the first extractor base 152 at the first end 122 of the test cell body 20, and a second extractor arm 260 is threadedly secured to the second extractor base 252 at the second end 124 of the test cell body 20. The first extractor arm 160 spans two corners of the test cell body 20 generally indicated at 171, 172. The second extractor arm 260 spans two other corners 173, 174 opposite the first two corners 171, 172.

A male threaded member 62 and a cooperating female threaded member 64 are provided at each of the four corners 171-174. For simplicity, the male and female threaded members 62, 64 are internally detailed only at the first corner 171 in FIG. 10, although similar cooperating threaded members are provided in corresponding locations of the other three corners 172-174. Thus, the first extractor arm 160 is movably secured to the first extractor base 152 by two of four cooperating sets of threaded members 62, 64, and the second extractor arm 260 is movably secured to the second extractor base 252 by the other two of four cooperating sets of threaded members. An exposed head (e.g. bolt head) 63 is optionally provided at each of the four corners 171-174, although only one bolt head 63 is required for rotation by a wrench 90.

A gear box 65 is provided near each corner 171-174. The gear boxes 65 are coupled by shafts 66, so that rotating the male threaded member 62 at any one of the corners 171, 172, 173, or 174 causes simultaneous rotation of the male threaded members at each of the other three corners. Thus, using the wrench 90 to rotate just one of the bolt heads 63—in this case, the bolt head 63 at the first corner 171—will rotate the male threaded member 62 at the first corner 171, and cause simultaneous rotation of the other three male threaded members 62 at the other three corners 172-174. By turning only one bolt head 63 with the wrench 90, a uniform upward force may be applied to extract the piston from the test cell body.

The terminology used herein is for the purpose of describing particular embodiments only and is not intended to be limiting of the invention. As used herein, the singular forms "a", "an" and "the" are intended to include the plural forms as well, unless the context clearly indicates otherwise. It will be further understood that the terms "comprises" and/or "comprising," when used in this specification, specify the presence of stated features, integers, steps, operations, elements, components and/or groups, but do not preclude the presence or addition of one or more other features, integers, steps, operations, elements, components, and/or groups thereof. The terms "preferably," "preferred," "prefer," "optionally," "may," and similar terms are used to indicate that an item, condition or step being referred to is an optional (not required) feature of the invention.

What is claimed is:

1. A proppant testing apparatus, comprising:
   a test cell body having an upper exterior surface, a lower exterior surface, and a test cavity extending through at least the upper exterior surface;
   an upper piston constrained to vertical reciprocation within the test cavity;
   a laterally-extending width bar coupled to the piston above the test cell body; and
   a portable piston extractor including an extractor base with an external channel for removably supporting the extractor base on the test cell body, the external channel including an upper flange and a lower flange connected by a web for removably receiving the test cell body between the upper and lower flanges, with the upper flange adjacent the upper exterior surface of the test cell body and the lower flange adjacent the lower exterior surface of the test cell body;
   an extractor arm movably coupled to the extractor base; and
   a drive mechanism configured for driving the extractor arm into vertical engagement with the width bar.

2. The proppant testing apparatus of claim 1, wherein the drive mechanism comprises:
   a first threaded member secured to the extractor base; and
   a second threaded member rotatably secured to the extractor arm and threadedly engaged with the first threaded member.

3. The proppant testing apparatus of claim 1, further comprising:
   a pressure port laterally extending through the test cell body to the test cavity on a face of the test cell body abutted by the flange of the extractor base;
   a pressure fitting sealingly connected to the pressure port; and
   a cutaway on the extractor base for receiving the pressure fitting without interference between the extractor base and the pressure fitting.

4. The proppant testing apparatus of claim 1, further comprising a cutaway on the extractor arm matching an outer profile of the upper piston.

5. The proppant testing apparatus of claim 1, further comprising:
   the test cell cavity vertically passing through the lower exterior surface; and
   a lower piston constrained to vertical reciprocation within the test cavity, the lower piston extending below the test cell body for supporting the test cell body on a working surface with the test cell body spaced above the working surface.

6. The proppant testing apparatus of claim 1, further comprising:
a guide hole in the extractor base laterally spaced from and parallel to the first threaded member; and
a guide pin secured to the extractor arm and slidingly received within the guide hole.

7. The proppant testing apparatus of claim 6, further comprising:
a horizontally extending guide slot defined by the test cell body, the guide slot receiving the extractor arm and constraining rotational and lateral movement of the extractor arm with respect to the extractor base over a range of vertical movement of the extractor arm.

8. A proppant testing apparatus, comprising:
a test cell body having an upper exterior surface, a lower exterior surface, and a test cavity extending through at least the upper exterior surface;
an upper piston constrained to vertical reciprocation within the test cavity;
a laterally-extending width bar coupled to the piston above the test cell body;
a portable piston extractor including an extractor base removably supportable on the test cell body;
an extractor arm movably coupled to the extractor base; and
a drive mechanism configured for driving the extractor arm into vertical engagement with the width bar, wherein the drive mechanism comprises a plurality of threaded members, each threaded member movably securing the extractor arm to the extractor base at one of a plurality of spaced-apart locations, a plurality of gear boxes, wherein each gear box is coupled to the threaded member at one of the spaced-apart locations, and one or more drive shafts coupling the gear boxes, such that rotation of one of the threaded members causes a corresponding rotation of all the threaded members to uniformly move the extractor arm with respect to the extractor base.

9. The proppant testing apparatus of claim 8, wherein the spaced-apart locations include four corners about the test cell body.

10. A method, comprising:
positioning a proppant sample between upper and lower compression dies in a test cavity of a test cell body;
positioning a seal between the compression dies and the test cell cavity to seal the proppant sample between the compression dies and the test cell cavity;
positioning an upper piston in the test cavity from above the test cell body;
forcibly urging the piston downward to compress the proppant sample;
subsequently supporting an extractor base on the test cell body and positioning a rigid extractor arm under a laterally-extending width bar coupled to the piston; and
threadedly engaging a threaded member on the extractor arm with a threaded member on an extractor base while preventing rotation of the extractor arm with respect to the extractor base, to urge the extractor arm into engagement with the laterally extending width bar and lift the piston with respect to the test cell body.

11. The method of claim 10, further comprising:
pressurizing the test cavity through a pressure fitting coupled to a pressure port on the test cell body during the step of forcibly urging the piston downward; and
positioning the extractor base with a cutaway on the extractor base receiving the pressure fitting without interference between the extractor base and the pressure fitting.

12. The method of claim 10, further comprising:
positioning a lower piston in the test cavity from beneath the test cell body;
capturing the proppant sample and compression dies between the first and lower pistons; and
supporting the test cell body on the lower piston with the test cell body spaced above the working surface with clearance between the extractor base and the working surface when the extractor base is supported on the test cell body.

13. The method of claim 10, further comprising positioning a guide pin secured to the extractor arm within a guide hole in the extractor base at a location laterally spaced from the first and second threaded members.

14. The method of claim 10, further comprising seating the extractor arm in a horizontally extending guide slot defined by the test cell body.

15. The method of claim 10, further comprising:
supporting a supplementary extractor base at another location on the test cell body and positioning a supplementary rigid extractor arm under a supplementary laterally-extending arm coupled to the piston; and
threadedly engaging a threaded member on the supplementary extractor arm with a threaded member on the supplementary extractor base while preventing rotation of the supplementary extractor arm with respect to the extractor base, to urge the extractor arm into engagement with the laterally extending width bar and lift the piston with respect to the test cell body.

16. The method of claim 15, alternately advancing the extractor arm and the supplementary extractor arm to progressively raise the piston.

17. A portable piston extractor for a proppant testing apparatus, comprising:
an extractor base including an external channel for removably supporting the extractor base on a test cell body, the external channel including an upper flange and a lower flange connected by a web for removably receiving the test cell body between the upper and lower flanges, with the upper flange adjacent an upper exterior surface of the test cell body and the lower flange adjacent a lower exterior surface of the test cell body;
an extractor arm movably coupled to the extractor base; and
a drive mechanism including a first threaded member secured to the extractor base and a second threaded member rotatably secured to the extractor arm and threadedly engaged with the first threaded member, for driving the extractor arm into vertical engagement with a width bar in response to rotation of the second threaded member with respect to the first threaded member.

18. The portable piston extractor of claim 17, further comprising:
a guide hole in the extractor base laterally spaced from and parallel to the first threaded member; and
a guide pin secured to the extractor arm and slidingly received within the guide hole.

* * * * *